United States Patent [19]

Tamai et al.

[11] Patent Number: 5,412,103
[45] Date of Patent: May 2, 1995

[54] PROCESS FOR PREPARING (1R,5S,6S)-2-[(6,7-DIHYDRO-5H-PYRAZOLO[1,2-A][1,2,4]TRIAZOLIUM-6-YL)]THIO-6-[(R)-1-HYDROXYETHYL]-1-METHYL-CARBAPENEM-3-CARBOXYLATE AND STARTING MATERIALS THEREOF

[75] Inventors: Satoshi Tamai, Kawasaki; Takao Abe, Tokorozawa; Yunosuke Nagase, Tokyo, all of Japan

[73] Assignee: Lederle (Japan), Ltd., Tokyo, Japan

[21] Appl. No.: 59,850

[22] Filed: May 11, 1993

Related U.S. Application Data

[60] Continuation of Ser. No. 902,727, Jun. 23, 1992, Pat. No. 5,241,703, which is a division of Ser. No. 633,540, Feb. 28, 1990.

[30] Foreign Application Priority Data

Oct. 12, 1990 [JP] Japan ................................. 2-272426
Oct. 12, 1990 [JP] Japan ................................. 2-272427
Oct. 12, 1990 [JP] Japan ................................. 2-272428

[51] Int. Cl.[6] ............................................ C07D 403/12
[52] U.S. Cl. ................................................. 548/365.1
[58] Field of Search ...................................... 548/365.1

[56] References Cited

U.S. PATENT DOCUMENTS

| | | | |
|---|---|---|---|
| 3,950,357 | 4/1976 | Kahan et al. | 540/350 |
| 4,249,934 | 2/1981 | Wakabayashi et al. | 548/264 |
| 4,320,132 | 3/1982 | Cecere et al. | 548/367 |
| 4,866,171 | 9/1989 | Kumagai et al. | 540/350 |
| 4,925,836 | 5/1990 | Kumagai et al. | 540/350 |
| 4,925,935 | 5/1990 | Kumagai et al. | 540/350 |

FOREIGN PATENT DOCUMENTS

| | | |
|---|---|---|
| 0168707 | 7/1985 | European Pat. Off. . |
| 0169410 | 1/1986 | European Pat. Off. . |
| 0289801 | 4/1988 | European Pat. Off. . |
| 2526358 | 1/1976 | Germany . |
| 3017875 | 11/1980 | Germany . |

OTHER PUBLICATIONS

Greene, Protective Groups in Organic Synthesis p. 213 (1981).

*Primary Examiner*—Robert Gerstl
*Attorney, Agent, or Firm*—Foley & Lardner

[57] ABSTRACT

Novel and improved simple process for preparing carbapenem compound, (1R,5S,6S)-2-[(6,7-dihydro-5H-pyrazolo [1,2-a][1,2,4]triazolium-6-yl)]thio-6-[(R)-1-hydroxyethyl]-1-methyl-carbapenem-3-carboxylate represented by the following formula:

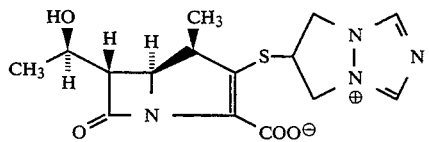

This compound may be prepared by using a mercapto reagent, 6,7-dihydro-6-mercapto-5H-pyrazolo[1,2-a][1,2,4]triazolium derivative of the following formula:

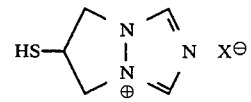

wherein X⊖ is an anion charge.

1 Claim, No Drawings

PROCESS FOR PREPARING (1R,5S,6S)-2-[(6,7-DIHYDRO-5H-PYRAZOLO [1,2-A][1,2,4]TRIAZOLIUM-6-YL)]THIO-6-[(R)-1-HYDROXYETHYL]-1-METHYL-CARBAPENEM-3-CARBOXYLATE AND STARTING MATERIALS THEREOF

This application is a continuation of Ser. No. 07/902,727, filed Jun. 23, 1992, U.S. Pat. No. 5,241,703 which is a Div of Ser. No. 07/633,540 filed Feb. 28, 1990.

BACKGROUND OF THE INVENTION

1. Field of the Invention

The present invention relates to a process for preparing (1R,5S,6S)-2-[(6,7-dihydro-5H-pyrazolo [1,2-a][1,2,4]triazolium-6-yl)]thio-6-[(R)-1-hydroxyethyl]-1-methyl-carbapenem-3-carboxylate represented by the following formula (I)

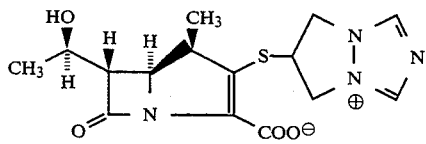

or a pharmacologically acceptable salt thereof.

2. Description of the Prior Art

Since the discovery of an antibiotic substance "thienamycin" from the nature [U.S. Pat. No. 3,950,357; J. Am. Chem. Soc., 100, 313 (1987)], many researches have been carried out to develop carbapenem antibiotics. As a result of the extensive study, there has been developed imipenem (INN) which is a practically available antibacterial agent for clinical use.

Recently, Kumagai et al. proposed (1R,5S,6S)-2-[(6,7-dihydro-5H-pyrazolo [1,2-a][1,2,4]triazolium-6-yl)]thio-6-[(R)-1-hydroxyethyl]-1-methyl-carbapenem-3-carboxylate of formula (I) above as carbapenem antibiotic. See U.S. Pat. Nos. 4,866,171; 4,925,836; and 4,925,935 (the entire specifications of these patents are incorporated herein by reference). This compound is carba-2-penem-3-carboxylic acid compound in which a β-methyl group is introduced at 1-position and 6,7-dihydro-5H-pyrazolo[1,2-a][1,2,4]triazolium-6-yl thio group which is represented by the following

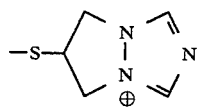

is introduced at 2-position of the carbapenem skelton. Owing to the presence of these specific substitutions, the compound of formula (I) has superior antibacterial activity with excellent chemical and physicochemical stabilities in living bodies, and is extremely stable against dehydropeptidase (DHP) known as a kidney enzyme.

The only synthesis for preparation of (1R,5S,6S)-2-[(6,7-dihydro-5H-pyrazolo [1,2-a][1,2,4]triazolium-6-yl)]thio-6-[(R)-1-hydroxyethyl]-1-methyl-carbapenem-3-carboxylate of formula (I) heretofore known in Kumagai et al. is from an imino intermediate. That is, according to Kumagai et al., the comound of formula (I) can be prepared by reacting a compound represented by formula (II):

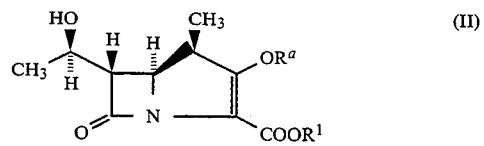

wherein $R^1$ is a carboxyl protecting group, and $R^a$ is an acyl group,
with a mercapto reagent represented by formula (VII):

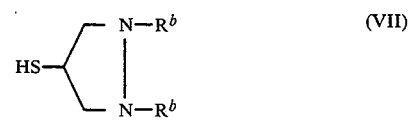

wherein $R^b$ is an amino protecting group,
to give a compound represented by formula (VIII):

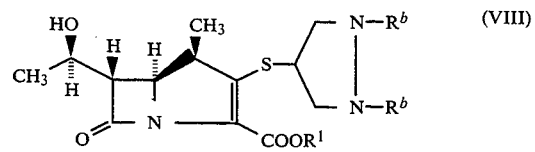

wherein $R^1$ and $R^b$ have the same meanings as above, and subjecting the compound of the formula (VIII) to removal of the protecting groups $R^1$ and $R^b$ to give the carbapenem compound of the formula (IX)

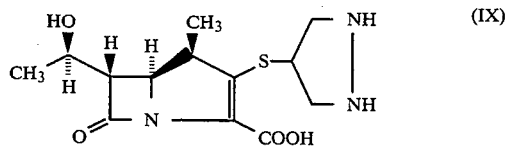

and then, reacting the resulting compound of formula (IX) with formimidic acid ester to give the carbapenem compound of formula (I).

One presumed course of reaction in the formation of the compound of formula (I) by the reaction of the compound of formula (IX) with the formimidic acid ester derivative is that by the reaction of the compound (IX) with the formimidic acid ester derivative, (1R,5S,6S)-6-[(R)-1-hydroxyethyl]-1-methyl-2-[(1,2-diiminomethyl)-4-pyrazolidinyl]thiocarbapenem-3-carboxylic acid of the following formula

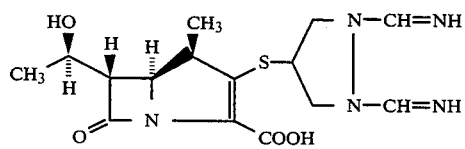

is formed as an intermediate, and this imino intermediate is transitory compound and undergoes cyclization reaction to form the compound of formula (I).

Finding a method for preparing the compound (1R,5S,6S)-2-[(6,7-dihydro-5H-pyrazolo [1,2-a][1,2,4]triazolium-6-yl)]thio-6-[(R)-1-hydroxyethyl]-1-methyl-carbapenem-3-carboxylate of formula (I)

through a method other than from the imino intermediate has been an objective of the research of the present inventors and their assignee since the discovery of the useful therapeutic indications of the compound (1R,5S,6S)-2-[(6,7-dihydro-5H-pyrazolo [1,2-a][1,2,4]triazolium-6-yl)]thio-6-[(R)-1-hydroxyethyl]-1-methyl-carbapenem-3-carboxylate. Despite the efforts of the researches of the assignee to find a way to make (1R,5S,6S)-2-[(6,7-dihydro-5H-pyrazolo [1,2-a][1,2,4]triazolium-6-yl)]thio-6-[(R)-1-hydroxyethyl]-1-methyl-carbapenem-3-carboxylate without going through the transitory intermediate, efforts heretofore have been unsuccessful. One apparent method for making (1R,5S,6S)-2-[(6,7-dihydro-5H-pyrazolo[1,2-a][1,2,4]triazolium-6-yl)]thio-6-[(R)-1-hydroxyethyl]-1-methyl-carbapenem-3-carboxylate is disclosed in Merck European Patent Application 168,707 (1986), that is discussed in detail in Kumagai et al. U.S. Pat. No. 4,866,171 at column 1, lines 22–49. There is a picture representation of the compound 6,7-dihydro-6-mercapto-5H-pyrazolo[1,2-a][1,2,4]triazolium halide which is a key compound for the synthesis in the European application. Nowhere in the European application is there any disclosure of the synthesis of a 6,7-dihydro-6-mercapto-5H-pyrazolo[1,2-a][1,2,4]triazolium halide nor is any method for the synthesis of a 6,7-dihydro-6-mercapto-5H-pyrazolo[1,2-a][1,2,4]triazolium halide available within the skill of the art.

SUMMARY OF THE INVENTION

The present invention provides a novel and improved simple process for preparing (1R,5S,6S)-2-[(6,7-dihydro-5H-pyrazolo [1,2-a][1,2,4]triazolium-6-yl)]thio-6-[(R)-1-hydroxyethyl]-1-methyl-carbapenem-3-carboxylate by using a key mercapto agent, 6,7-dihydro-6-mercapto-5H-pyrazolo[1,2-a][1,2,4]triazolium derivative.

In accordance with the invention, there is provided a process for preparing (1R,5S,6S)-2-[(6,7-dihydro-5H-pyrazolo [1,2-a][1,2,4]triazolium-6-yl)]thio-6-[(R)-1-hydroxyethyl]-1-methyl-carbapenem-3-carboxylate of the following formula

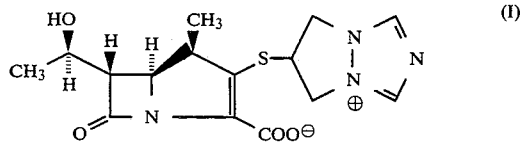

or a pharmacologically acceptable salt thereof; which comprises reacting a compound represented by the following formula

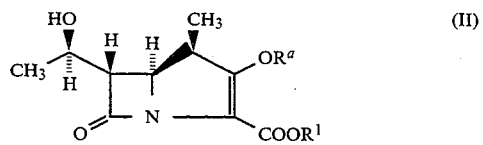

wherein $R^1$ is a carboxyl protecting group, and
$R^a$ is an acyl group,
with 6,7-dihydro-6-mercapto-5H-pyrazolo[1,2-a][1,2,4]triazolium derivative represented by the following formula

wherein $X^{\ominus}$ is an anion charge,
to give a compound represented by the following formula

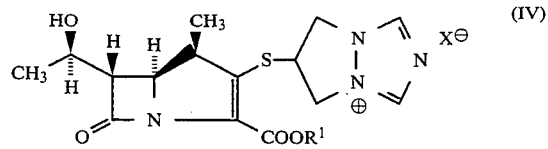

wherein $R^1$ and $X^{\ominus}$ have the same meanings as above, and then, subjecting the resulting compound of formula (IV) to removal of the carboxyl protecting group to give the carbapenem compound represented by formula (I).

In accordance with a second aspect of the invention, there is provided 6,7-dihydro-6-mercapto-5H-pyrazolo[1,2-a][1,2,4]triazolium derivative represented by the following formula

wherein $X^{\ominus}$ is an anion charge.
This compound of formula (III) is a key mercapto reagent as a starting material for synthesis of the present invention.

For the above purpose of the invention, the compound of formula (III) may be prepared by reacting pyrazolidine-4-yl-disulfide represented by the following formula

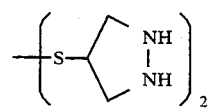

with formimidic acid ester to give 6,7-dihydro-5H-pyrazolo[1,2-a][1,2,4]triazolium-6-yl-disulfide represented by the following formula

wherein $X^{\ominus}$ is is the same meaning as above,
and then, reducing the resulting compound of formula (V) to form the compound represented by the formula (III).

Therefore, in accordance with further aspect of the present invention, there are provided compounds represented by formula (V) and (VI), respectively.

Furthermore, the present invention provides a process for preparing the compound of formula (III).

DETAILED DESCRIPTION OF THE INVENTION

The remarkable characteristics of the carbapenem compound according to the present invention are that the substituent at 2-position of the carbapenem skelton is a 6,7-dihydro-5H-pyrazolo[1,2-a][1,2,4]triazolium-6-yl thio group and that it has superior antibacterial activity and resistance to DHP.

In accordance with the present invention, the carbapenem compound represented by formula (I) may be prepared by a process described below.

The carbapenem compound of formula (I) can be prepared by (a) reacting pyrazolidine-4-yl-disulfide represented by the following formula

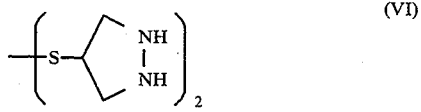

with formimidic acid ester to give a 6,7-dihydro-5H-pyrazolo[1,2-a][1,2,4]triazolium-6-yl-disulfide represented by the following formula

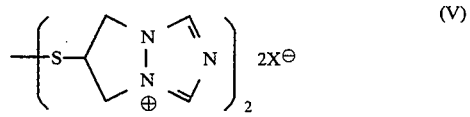

wherein $X^{\ominus}$ is an anion charge, (b) reducing the resulting compound of formula (V) to form a 6,7-dihydro-6-mercapto-5H-pyrazolo[1,2-a][1,2,4]triazolium derivative represented by the following formula

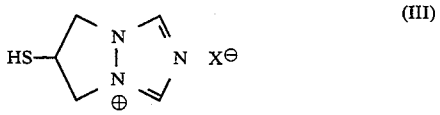

wherein $X^{\ominus}$ has the same meaning as above, (c) reacting the resulting compound of formula (III) with a compound represented by the following formula

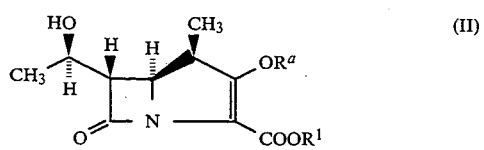

wherein $R^1$ is a carboxyl protecting group, and $R^a$ in an acyl group,
to give a compound represented by the following formula

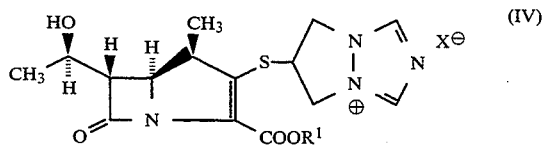

wherein $R^1$ and $X^{\ominus}$ have the same meanings as above, (d) then, subjecting the resulting compound of formula (IV) to removal of the carboxyl protecting group to give the carbapenem compound represented by formula (I)

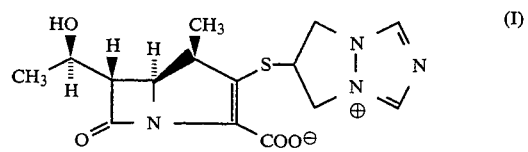

More specifically, the carbapenem compound represented by formula (I) may be prepared in such a manner as described in detail below.

In the specification of the present application, the term "lower" qualifying a group of a compound means that the group or compound so qualified has from 1 to 7, preferably from 1 to 4, carbon atoms.

The term "lower alkyl" referred to herein stands for a straight-chained or branched-chain hydrocarbon group having preferably from 1 to 6 carbon atoms and may include, for example, methyl, ethyl, n-propyl, isopropyl, n-butyl, isobutyl, sec-butyl, tert.-butyl, n-pentyl, isopentyl, n-hexyl, isohexyl or the like.

The term "carboxyl protecting group" referred to herein stands for any group capable of protecting the carboxyl group of the compound involved without adversely affecting any other substituents and the reactions that follow and may include, for example, an ester residue such as a lower alkyl ester residue including, for example, methyl ester, ethyl ester, n-propyl ester, isopropyl ester, n-, iso-, sec- or tert.-butyl ester, n-hexyl ester or the like; an aralkyl ester residue including, for example, benzyl ester, n-nitrobenzyl ester, o-nitrobenzyl ester, p-methoxybenzyl ester or the like; and a lower aliphatic acyloxymethyl ester residue including, for example, acetoxymethyl ester, propionyloxymethyl ester, n- or iso-butyryloxymethyl ester, pivaloyloxymethyl ester or the like.

The term "acyl group" referred to herein stands for, in a narrower sense, a moiety obtainable by removing the hydroxyl group from the carboxyl group of an organic carboxylic acid as well as, in a broader sense, any acyl group derived from an organic sulfonic acid or an organic phosphoric acid. Such an acyl group may include, for example, a lower alkanoyl group such as acetyl, propionyl, butyryl or the like, a (halo)lower alkyl sulfonyl group such as methanesulfonyl, trifluoromethanesulfonyl or the like; a substituted or unsubstituted arylsulfonyl group such as benzenesulfonyl, p-nitrobenzenesulfonyl, p-bromo-benzenesulfonyl, toluenesulfonyl, 2,4,6-triisopropylbenzenesulfonyl or the like; and diphenylphosphoryl.

The term "amino protecting group" referred to herein stands for groups usually employed in peptide chemistry, for example, aromatic acyl groups such as phthaloyl, benzoyl, benzoyl substituted by halogen, nitro or a lower alkyl of 1 to 4 carbon atoms (e.g. chlorobenzoyl, p-nitrobenzoyl, p-tert-butylbenzoyl, toluoyl), naphthoyl; phenylacetyl; phenoxyacetyl; benzenesulfonyl; benzenesulfonyl substituted by a lower alkyl of 1 to 4 carbon atoms (e.g. p-tert-butylbenzenesulfonyl, toluenesulfonyl); acyl derived from aliphatic or halogenated aliphatic carboxylic acid such as acetyl, valeryl, caprylyl, n-decanoyl, acyloyl, pivaloyl, halogenoacetyl (e.g. monochloroacetyl, monobromoacetyl, dichloroacetyl, trichloroacetyl); camphorsulfonyl; methanesulfonyl; esterified carboxyl groups such as ethoxycarbonyl, tert-butyloxycarbonyl, isobornyloxycarbonyl, phenyloxycarbonyl, trichloroethoxycarbonyl, benzyloxycarbonyl, etc.; carbamoyl groups such as methylcarbamoyl, phenylcarbamoyl, naphthylcarbamoyl, etc.; and the corresponding thiocarbamoyl groups.

The term "anion charge" referred to herein stands for a counterpart anion charge to a quaternary ammonium cation charge, and may include, for example, hydroxy anion; alkoxy anion such as methoxy anion, ethoxy anion; halogeno anion such as chloride anion, bromide anion, iodide anion, fluoride anion; and "acid anion residue" described below.

The term "acid anion residue" referred to herein may include acidic anion moiety obtainable by removing hydrogen atom from the organic acid, for example, a lower fatty acid such as acetic acid, propionic acid, butyric acid or trifluoroacetic acid; a substituted or unsubstituted aryl acid such as benzoic acid, p-nitrobenzoic acid or the like; a (halo)lower alkylsulfonic acid such as methanesulfonic acid or trifluoromethanesulfonic acid; a substituted or unsubstituted arylsulfonic acid such as benzenesulfonic acid, p-nitrobenzenesulfonic acid, p-bromobenzenesulfonic acid, toluenesulfonic acid, 2,4,6-triisopropylbenzenesulfonic acid or the like; substituted or unsubstituted arylphosphoric acid such as diphenylphosphoric acid; and inorganic acid such as nitrous acid, nitric acid, sulfuric acid, hydrochloric acid, hydrobromic acid, perchloric acid, fluorobromic acid or the like.

The mercapto reagent, 6,7-dihydro-6-mercapto-5H-pyrazolo[1,2-a][1,2,4]triazolium derivative represented by formula (III) to be employed as a starting compound in the process for manufacturing the carbapenem compound of formula (I) may be prepared in accordance with the following Reaction Scheme A.

REACTION SCHEME A

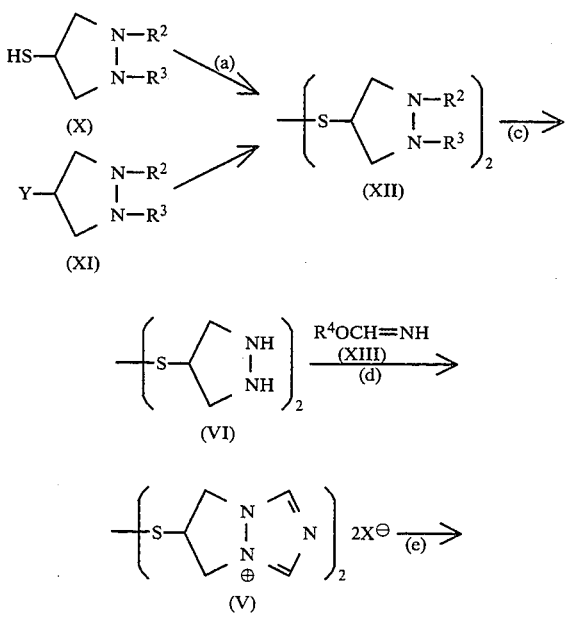

-continued
REACTION SCHEME A

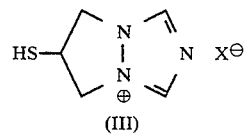

wherein $R^2$ and $R^3$ are, independently each other, a hydrogen atom or an amino protecting group ($R^2$ and $R^3$ are not both hydrogen); $R^4$ is a lower alkyl group; and Y is an acid anion residue.

The step (a) involves the reaction of the oxidation of 4-mercaptopyrazolidine derivative of formula (X) to give pyrazolidine-4-yl-disulfide derivative of formula (XII).

The oxidizing reaction of 4-mercaptopyrazolidine derivative of formula (X) may be carried out in such a manner as known oxidizing reaction of thiol compound in the organic chemical field. For example, the reaction can be carried out in a solvent inert in the reaction such as chloroform, dichloromethane or the like, in the presence of an oxidizing reagent such as hydrogen peroxide, per-acid, copper (II) chloride, bromine, iodine or halosuccinimide. An air-oxidizing reaction (in the presence of a base) may also be used for this purpose. Preferred reaction condition may be achieved by using iodine as the oxidizing reagent or the air-oxidizing in the presence of iron powder.

The step (b) involves the reaction of 4-substituted pyrazolidine derivative of formula (XI) with sulfur compound to give pyrazolizine-4-yl-disulfide derivative of formula (XII).

The acidic anion residue for symbol "Y" in the compound of formula (XI) is acidic moiety obtainable by removing hydrogen atom from the acid mentioned before, and preferably Y may be halogen atom such as chlorine or bromide; or sulfonic acid residue such as methanesulfonyloxy residue, toluenesulfonyloxy residue or trifluoromethanesulfonyloxy residue.

The sulfur compound to be used in this reaction may be sulfur powder, hydrogen sulfide, sodium sulfide or the like.

The step (c) is a step of elimination of the amino protecting groups $R^2$ and $R^3$ from the compound of formula (XII) obtained by the step (a) or (b) above to give pyrazolidine-4-yl-disulfide of formula (VI).

The removal of the protecting groups $R^2$ and $R^3$ may be made by a reaction known per se for removing a protective group, such as solvolysis or hydrogenolysis. In a typical reaction, the compound represented by formula (XII) may be treated, for instance, in a mixture of solvents such as tetrahydrofuran-water, tetrahydrofuran-ethanol-water, dioxane-water, dioxane-ethanol-water, n-butanol-water or the like containing morpholino-propane sulfonic acid-sodium hydroxide buffer solution (pH 7), a phosphate buffer solution (pH 7), dipotassium phosphate, sodium bicarbonate or the like, using hydrogen under 1 to 4 atmospheric pressures, in the presence of a catalyst for hydrogenation such as platinum oxide, palladium-activated carbon or palladium hydroxide-activated carbon at temperatures ranging from approximately 0° C. to approximately 50° C. for approximately 0.25 to approximately 4 hours.

As a result, the compound of formula (VI) may be obtained as di or tetra acid addition salt by treating with an acid, and may include the following acid addition salt; pyrazolidine-4-yl-disulfide di or tetra hydrochloride salt, di or tetra hydrobromide salt, di or tetra hydroiodide salt, di or tetra trifluoroacetic acid salt, di or tetra trifluoromethanesulfonic acid salt, and di or tetra toluenesulfonic acid salt.

The step (d) involves the reaction of pyrazolidine-4-yl-disulfide of formula (VI) with a formimidic acid ester derivative of formula (XIII) to give 6,7-dihydro[1,2-a][1,2,4]triazolium-6-yl-disulfide represented by formula (V).

The reaction may be carried out by reacting the compound of formula (VI) with the formimidic acid ester derivative such as ethyl formimidate hydrochloride, methyl formimidate hydrochloride or benzyl formimidate hydrochloride in an inert solvent such as water, alcohol, tetrahydrofuran or acetone. The pH of the reaction medium may be adjusted from about 6 to about 8 by adding a base such as sodium hydrogen carbonate, potassium hydrogen carbonate, sodium carbonate, potassium carbonate, sodium hydroxide, potassium hydroxide, sodium acetate, potassium acetate or the like.

The quantity of the formimidic acid ester derivative of formula (XIII) is not critical and may vary appropriately in a range generally from approximately 1 mole to approximately 20 moles, preferably from 4 moles to 12 moles, per mole of the compound (V). The reaction temperature is not limited to a particular range and may vary from about −78° C. to about room temperature, preferably from about −20° C. to about 10° C. The reaction may be finished under such conditions as described above generally in approximately 5 minutes to approximately 1 hour.

6,7-Dihydro-5H-pyrazolo[1,2-a][1,2,4]triazolium-6-yl-disulfide of formula (V) may be obtained from the reaction mixture as crystalline form in this reaction.

The step (e) is a step by which 6,7-dihydro-6-mercapto-5H-pyrazolo[1,2-a][1,2,4]triazolium derivative of formula (III) may be prepared by reducing the compound of formula (V) obtained by, the step (d) above.

The reducing reaction may be conducted in accordance with known reaction condition employed for cleavage of sulfur-sulfur bond of disulfide compound, for example, reduction with trialkylphosphine such as trimethylphosphine, triethylphosphine, tributylphosphine; triarylphosphine such as triphenylphosphine; reduction with metal; or reduction with sodium borohydride, lithium aluminum hydride or lithium triethylborohydride. Particularly, the reduction with tributylphosphine may be preferably employed. The reaction is preferably conducted in an inert solvent such as water; alcohol such as methanol, ethanol or isopropanol; ether such as ethyl ether, tetrahydrofuran or dioxane; or the mixture solvent thereof in the presence of the reducing reagent.

The reaction temperature and time are not limited to a particular range and may vary according to the reducing reagent to be used. Usually, the reaction temperature may be in a range from about −20° C. to about 100° C., preferably from about room temperature to about 50° C. and the reaction time may be from about 10 minutes to about 10 hours. After reducing reaction, 6,7-dihydro-6-mercapto-5H-pyrazolo[1,2-a][1,2,4]triazolium derivative of formula (III) may be obtained as a quaternary ammonium salt of formula (III) by using conventional manner such as distillation, extraction, lyophilization, etc.

6,7-Dihydro-6-mercapto-5H-pyrazolo[1,2-a][1,2,4]triazolium chloride, bromide, iodide, trifluoroacetate, methanesulfonate or p-toluenesulfonate can be obtained by the reaction above.

The carbapenem compound of the present invention, (1R,5S,6S)-2-[(6,7-dihydro-5H-pyrazolo[1,2-a][1,2,4]triazolium-6-yl)]thio-6-[(R)-1-hydroxyethyl]-1-methyl-carbapenem-3-carboxylate represented by formula (I) may be prepared in accordance with the following Reaction Scheme B.

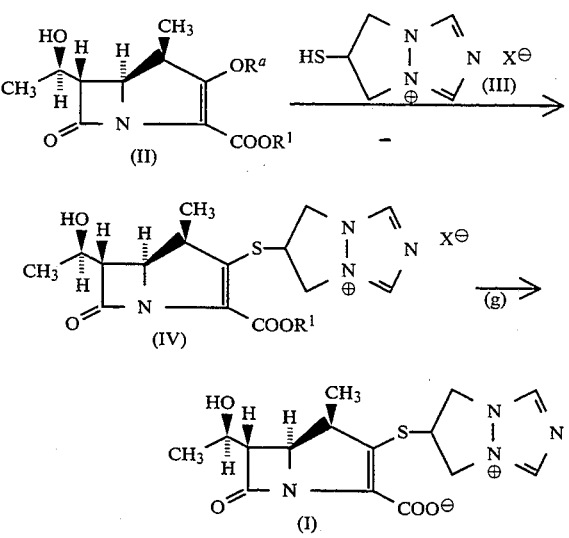

REACTION SCHEME B wherein $R^1$, $R^a$ and $X^\ominus$ have the same meanings as above.

The step (f) involves the reaction of a compound of formula (II) with mercapto reagent, that is, 6,7-dihydro-6-mercapto-5H-pyrazolo[1,2-a][1,2,4]triazolium derivative of formula (III), to give a compound of formula (IV).

The reaction of the compound of formula (II) with the mercapto reagent of formula (III) may be carried out, for instance, by reacting the compound of formula (II) with the mercapto reagent of formula (III) in an excess amount ranging from about an equimolar amount to approximately 1.5 molar amount in an appropriate solvent such as tetrahydrofuran, dichloromethane, dioxane, dimethylformamide, dimethylsulfoxide; acetonitrile, hexamethylene phosphoramide or the like, preferably in the presence of a base such as sodium hydrogen carbonate, potassium carbonate, triethylamine, diisopropylethyl amine or the like at a temperature range from approximately −40° C. to approximately 25° C. for approximately 30 minutes to approximately 24 hours.

The reaction described above provides the carbapenem compound represented by formula (IV) in which the carboxyl group at the 3-position thereof is protected by the carboxyl protecting group $R^1$. The removal of the protecting group $R^1$ may be made by a reaction known per se for removing a protective group, such as solvolysis or hydrogenolysis. In a typical reaction, the compound represented by formula (IV) may be treated, for instance, in a mixture of solvents such as tetrahydrofuran-water, tetrahydrofuran-ethanol-water, dioxane-water, dioxane-ethanol-water, n-butanol-water or the like containing morpholino-propane sulfonic acid-sodium hydroxide buffer solution (pH 7), a phosphate buffer solution (pH 7), dipotassium phosphate, sodium bicarbonate or the like, using hydrogen under 1 to 4 atmospheric pressures, in the presence of a catalyst for hydrogenation such as platinum oxide, palladium-activated carbon or palladium hydroxide-activated carbon at temperatures ranging from approximately 0° C. to approximately 50° C. for approximately 0.25 to approximately 4 hours.

As a result, (1R,5S,6S)-2-[(6,7-dihydro-5H-pyrazolo[1,2-a][1,2,4]triazolium-6-yl)]thio-6-[(R)-1-hydroxyethyl]-1-methyl-carbapenem-3-carboxylate represented by formula (I) is produced.

The carbapenem compound of formula (I) is extremely stable against dehydropeptidase (DHP) and has superior antibacterial activity.

The production of the carbapenem compounds of the formula (I) according to the present invention will be described more in detail by way of working examples.

In the following description, the following symbols are used to have the particular meanings.

Ac: acetyl group
Z: benzyloxycarbonyl group
PNB: p-nitrobenzyl group

EXAMPLE 1

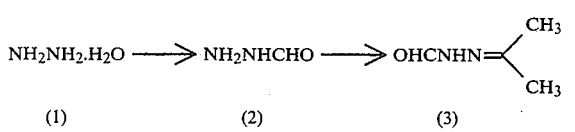

(1)      (2)      (3)

To a solution of 377 g of hydrazine monohydrate in 760 ml of ethanol was added dropwise 726 ml of ethylformate at 0° C. over 1 hour, and the reaction mixture was stirred for 30 minutes at the same temperature and for 14 hours at room temperature. Then the reaction mixture was added to 1011 ml of acetone over 30 minutes, and the resultant solution was stirred for 30 minutes at room temperature. After the reaction, the solvent was removed under reduced pressure to give 721 g (96%) of Compound (3) as a white solid.

NMR(CDCl$_3$) δ: 1.92(S,3H), 2.00(s,3H), 8.65(d,1H,J=9.9 Hz)

EXAMPLE 2

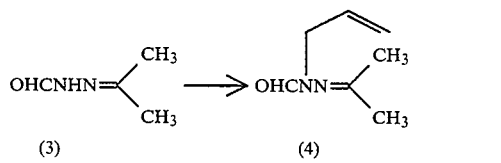

(3)           (4)

To a solution of 1 g of Compound (3) in 10 ml of methanol was added 2.12 g of 28% sodium methoxide-methanol solution at room temperature, and the mixture was stirred for 1 hour, and then refluxed for 30 minutes. Then, 1 ml of allyl bromide was added to the reaction mixture at room temperature and the mixture was stirred for 1 hour at the same temperature, and then refluxed for 30 minutes. After the reaction, the mixture was cooled to room temperature, and neutralized by adding formic acid. After the reaction solvent was removed under reduced pressure, the resulting residue was purified by column chromatography to give 933 mg (67%) of Compound (4) as a colorless oil.

NMR(CDCl$_3$) δ: 1.86(S,3H), 2.13(s,3H), 4.08–4.24(m,2H), 5.17–5.37(m,2H), 5.66–5.91(m,1H), 7.93–8.07(m, 1H)

EXAMPLE 3

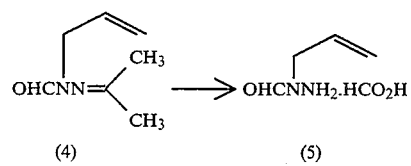

(4)           (5)

3.7 g of Compound (4) was dissolved in 37 ml of formic acid, and the solution was stirred for 6 hours at room temperature. After the reaction, the solvent was removed under reduced pressure and the residue was purified by column chromatography to give 3.1 g (80%) of Compound (5) as a pale yellowish oil.

NMR(CDCl$_3$) δ: 1.79(brs,1H), 4.1–4.3(m,2H), 5.2–5.5(m,2H), 5.6–6.0(m,1H), 7.9–8.4(m,3H)

EXAMPLE 4

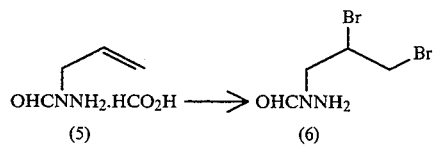

(5)           (6)

To a solution of 3.1 g of Compound (5) in 15 ml of dichloromethane was added a solution of 2.2 g of sodium bromide monohydrate in 6 ml of methanol. To this mixture, 2.16 ml of bromide in 5 ml of dichloromethane was added dropwise over 30 minutes under ice-cooling, and the resulting mixture was stirred for 30 minutes at room temperature. After the reaction, 6 ml of aqueous solution of 7.1 g of NaHCO$_3$ and 5 ml of saturated aqueous sodium sulfite were added to the reaction mixture and stirred for 10 minutes under ice-cooling. The mixture was extracted with ethyl acetate and the organic layer was dried over Na$_2$SO$_4$. After the solvent was removed off under reduced pressure, the resulting residue was purified by column chromatography to give 5.24 g (95%) of Compound (6) as a colorless oil.

NMR(CDCl$_3$) δ: 1.96(brs,1H), 3.4–4.5(m,5H), 8.0–8.4(m,2H)

EXAMPLE 5

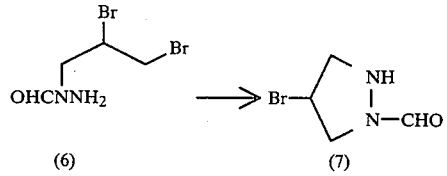

(6)           (7)

5.5 g of K$_2$CO$_3$ was added to an ice-cooled solution of 5.2 g of Compound (6) in 26 ml of acetonitrile and the mixture was stirred for 1 hour at room temperature. After the removal of the precipitate, the solvent was removed under reduced pressure. The residue was purified by column chromatography to give 3.2 g (90%) of Compound (7) as a pale yellowish oil.

NMR(CDCl$_3$) δ: 1.68(brs,1H), 3.8–4.6(m,5H), 8.50(s,1H)

EXAMPLE 6

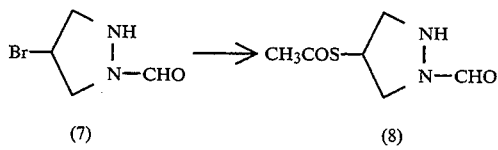

To a solution of 3.0 g of Compound (7) in 15 ml of acetonitrile was added 2.4 g of potassium thioacetate, and the mixture was stirred for 5 hours at room temperature. After removal of the precipitate by filtration, the solvent was removed under reduced pressure. The resulting residue was purified by column chromatography to give 2.65 g (91%) of Compound (8) as a pale yellowish oil.

NMR(CDCl$_3$) δ: 1.61(brs,1H), 2.37(m,3H), 3.4–4.2(m,5H), 8.42(s,1H)

EXAMPLE 7

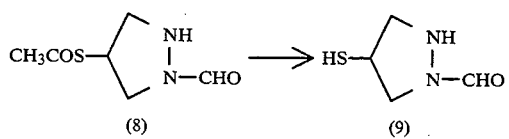

To a solution of 2.5 g of Compound (8) in a mixture of 10 ml of dichloromethane:methanol (4:1) was added 2.9 g of 28% sodium methoxide-methanol solution under ice-cooling, and the mixture was stirred for 5 minutes under the same temperature. Then, formic acid was added to the reaction mixture for neutralization and the precipitate was removed off by filtration. The solvent was removed, and the resulting residue was purified by column chromatography to give 1.7 g (90%) of Compound (8) as a pale yellowish oil.

NMR(CDCl$_3$) δ: 1.83(d,1H,J=5.3 Hz), 2.8–3.0(m,2H), 3.2–3.4(m,2H), 3.9–4.1(m,1H), 8.45(s,1H)

EXAMPLE 8

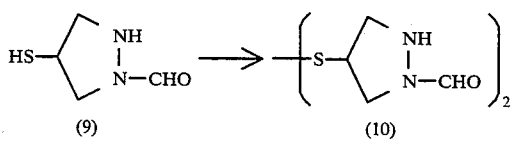

1.7 g of Compound (9) was dissolved in a mixture solution of 5.1 ml of methanol:water (2:1). To this solution, 2.6 g of KHCO$_3$ and 340 mg of Fe(II)Cl$_2$.6H$_2$O were added and the mixture was stirred overnight at room temperature. After removal of the precipitate, the solvent was removed under reduced pressure and the residue was purified by column chromatography to give 1.5 g (90%) of Compound (10) as a colorless oil.

NMR(CDCl$_3$) δ: 4.0–4.3(m,2H), 5.2–5.5(m,2H), 5.6–5.9(m,1H), 8.0–8.3(m,2H)

EXAMPLE 9

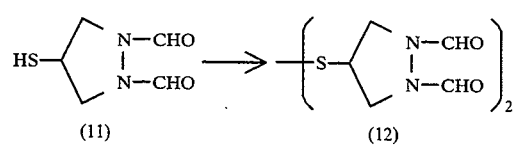

To a solution of 8.12 g of Compound (11) in 75 ml of methanol:water (2:1) mixture were added 10.2 g of KHCO$_3$ and 1.37 g of Fe(II)Cl$_2$.6H$_2$O, and the mixture was stirred for 8 hours at room temperature. After the reaction, the precipitate was removed off by filtration, and the solvent was concentrated under reduced pressure. The residue was dissolved in chloroform and dried over sodium sulfate. The solvent was removed under reduced pressure to give 7.25 g (90%) of Compound (12) as a colorless oil.

NMR(CDCl$_3$) δ: 3.10–4.00(m,8H), 4.55–4.75(m,2H), 8,42(s,4H)

EXAMPLE 10

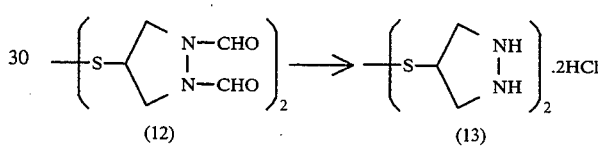

7.25 g of Compound (12) was dissolved in a mixture solution of 11.4 ml of conc. HCl and 103 ml of methanol and the mixture was stirred for 6 hours at room temperature. After reaction, the precipitate was collected by filtration, and dried in vacuo to yield 5.08 g (85%) of Compound (13) as a white solid.

NMR(CDCl$_3$) δ: 3.39(dd,4H,J=3.8 Hz,13.0 Hz), 3.59(dd,4H,J=6.76 Hz,13.0 Hz), 3.94–4.02(m,2H)

EXAMPLE 11

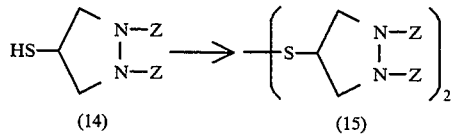

To a solution of 11.4 g of Compound (14) in 20 ml of dichloromethane where added 0.56 ml of triethylamine and 508 mg of iodine, and the reaction mixture was stirred for 10 minutes at room temperature. After the reaction, the mixture was washed with a sodium thiosulfite solution and a saturated sodium chloride solution, and then dried over sodium sulfate. After removal of the solvent under reduced pressure, the resulting residue was purified by silica gel column chromatography to give 939 mg (85.2%) of Compound (15) as a pale yellowish solid.

NMR(CDCl$_3$) δ: 3.25(m,2H), 3.40(m,2H), 3.70(m,2H), 4.10(m,4H), 5.16(s,8H), 7.30(s,20H)

EXAMPLE 12

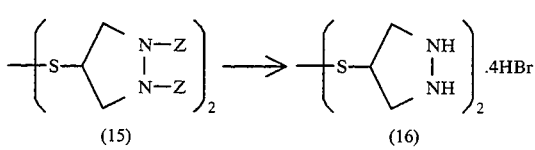

A mixture solution of 742 mg of Compound (15) in 3.1 g of hydrobromic acid-acetic acid solution (25%) was stirred for 4 hours at room temperature. After the reaction, the resulting precipitate was collected by filtration, and washed with 10 ml of ethyl acetate. This precipitate was treated with methanol to give 420 mg (79%) of Compound (16) as a pale brownish solid.

NMR($D_2O$) δ: 3.50(4H,m), 3.53–3.85(6H,m)

EXAMPLE 13

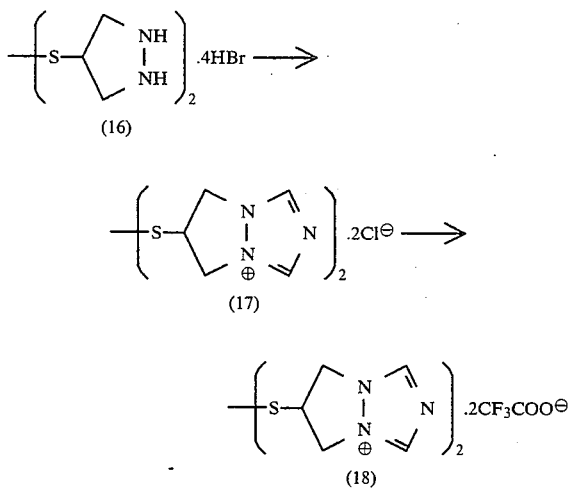

852.2 mg of $KHCO_3$ was added to an ice-cooled solution of 568 mg of Compound (16) in 30 ml of water to adjust the pH of the solution to 7.10. Then, 2.112 g of ethyl formimidate hydrochloride was added to this solution and the reaction mixture was stirred for 10 minutes under the same condition. After the pH of the reaction mixture was adjusted to 5.5 with 1N-HCl, the mixture was washed with 50 ml of ethyl acetate. The aqueous solution was concentrated to dryness under reduced pressure, and 30 ml of methanol was added to the residue. After removal of the precipitate by filtration, the solvent was removed and the resulting residue was purified by SP-207 column chromatography and the eluent was lyophilized to give Compound (17).

This Compound (17) obtained by the above step was dissolved in 10 ml of methanol and treated with 1 ml of trifluoroacetic acid. The solvent was removed under reduced pressure to give 317.2 mg (58.3%) of Compound (18) as a white crystal.

NMR($D_2O$) δ: 4.80–5.00(4H,m), 5.00–5.16(6H,m), 9.05(4H,s)

EXAMPLE 14

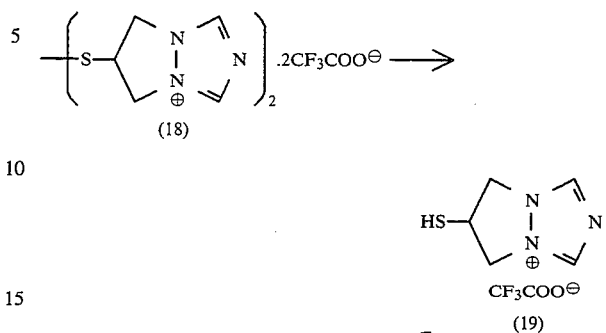

To a solution of Compound (18) in 6 ml of water-tetrahydrofuran (1:1) was added 0.082 ml of tri-n-butylphosphine under ice-cooling, and the mixture was stirred for 1 hour at the same temperature. After the reaction, 10 ml of water was added to the reaction mixture and the mixture was washed with dichloromethane and ethyl acetate. The aqueous layer was lyophilized to give 102.2 mg (90.9%) of Compound (19) as a white solid.

NMR($D_2O$) δ: 4.50–4.70(2H,m), 5.00–5.20(3H,m), 9.00(2H,s)

EXAMPLE 15

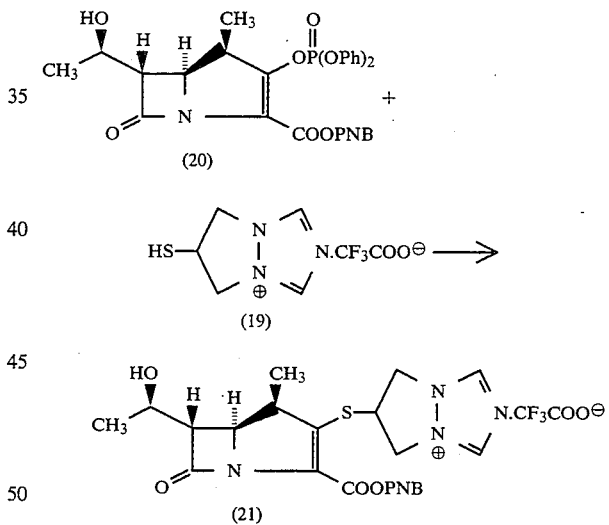

To an ice-cooled solution of 85.5 mg of Compound (19) and 199.6 mg of Compound (20) in 3 ml of anhydrous acetonitrile was added dropwise 0.06 ml of diisopropylethylamine, and the mixture was stirred for 1 hour under the same temperature. After the reaction, the solvent was removed under reduced pressure and the resulting residue was dissolved in 20 ml of ethylacetate and then the solution was centifuged for 5 minutes at 3,000 rpm. After centrifugation, the supernatant was decanted. The centrifugation and decantation was repeated three times and each supernatant was collected and concentrated under reduced pressure. The resulting residue was dissolved in 20 ml of chloroform and the mixture was centrifuged, and the supernatant was decanted off. Then, every residue obtained by the above centrifugation was collected and dissolved in methanol.

After removal of methanol under reduced pressure, 134.8 mg (67%) of Compound (21) was obtained as a pale yellowish oil.

NMR(CD$_3$OD) δ: 1.32(d,6H,J=6.0 Hz), 3.35(m,1H), 3.65(m,1H), 4.20(m,1H), 4.42(m,1H), 4.60–4.90(m,2H), 5.1–5.3(m,3H), 5.36(ABq,2H,J=13.7 Hz), 7.67 (d,2H, J=8.5 Hz), 8.21(d,2H,J=8.5 Hz), 9.07(s,1H), 9.08(S,1H)

EXAMPLE 16

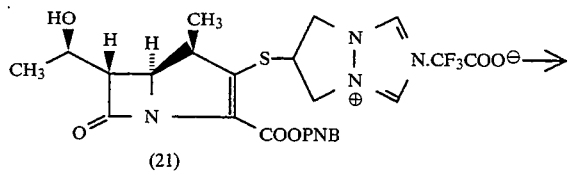
(21)

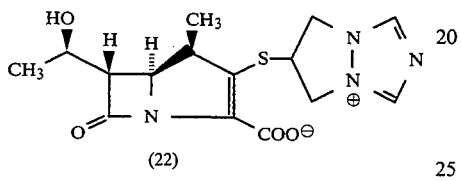
(22)

To a solution of 84.9 mg of Compound (21) in 2.5 ml of 0.1M acetate buffer and 2.5 ml of n-butanol was added 25 mg of 10% palladium-carbon, and the catalytic hydrogeneration was carried out at room temperature for 1 hour under a pressure of 4.0 atmospheres. After removal of the catalyst, the catalyst was washed with 20 ml of water. The solvent was combined and the pH of the solution was adjusted to 4.8–5.6 by adding 1N-NaOH solution and washed with 20 ml of n-butanol. The solvent was concentrated to 5 ml under reduced pressure, and the resulting residue was purified by SP-207 column chromatography and recrystallized from ethanol to give 30 mg (60%) of Compound (21) as a white crystal.

NMR(D$_2$O) δ: 1.29(d,3H,J=7.3 Hz), 1.33(d,3H,J=6.3 Hz), 3.44(dq,1H,J=7.3, 9.5 Hz), 3.56(dd, 1H,J=2.9, 6.2 Hz), 4.30(quintet,1H,J=6.2 Hz), 4.34(dd,1H,J=2.9, 9.5 Hz), 4.75–4.84(m,2H), 5.08–5.17(m,2H), 4.98–5.04(m,1H), 9.06(s,1H), 9.07(s,1H)

What we claim is:

1. A pyrazolidine-4-yl-disulfide represented by the following formula

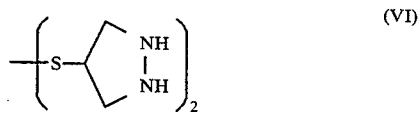
(VI)

or salt thereof.

* * * * *